United States Patent [19]

Fedorov et al.

[11] Patent Number: 5,286,829

[45] Date of Patent: * Feb. 15, 1994

[54] BIOCOMPATIBLE POLYMER MATERIAL AND A PROCESS FOR PRODUCING SAME

[76] Inventors: Svyatoslav N. Fedorov, pereulok Dostoevskogo, 1/21, kv. 32; Sergei N. Bagrov, ulitsa Smolnaya, 21, korpus 2, kv. 368; Alexei V. Osipov, Leningradskoe shosse, 50, kv. 233; Elena A. Linnik, ulitsa Deguninskaya, 17, kv. 36; Irina A. Maklakova, ulitsa 800-letia Moskvy, 6, kv. 213; Alexei N. Kosmynin, ulitsa Oktyabrskaya, 60, korpus 2, kv. 25; Evgeny V. Larionov, ulitsa Seligerskaya, 25, kv. 5, all of Moscow, U.S.S.R.

[ * ] Notice: The portion of the term of this patent subsequent to Nov. 15, 2009 has been disclaimed.

[21] Appl. No.: 549,452

[22] Filed: Jul. 6, 1990

[30] Foreign Application Priority Data

Oct. 13, 1989 [SU] U.S.S.R. .............................. 4745668

[51] Int. Cl.$^5$ .......................... C08H 5/00; C08F 2/46; C08G 63/48; C08G 63/91

[52] U.S. Cl. .................... 527/201; 527/202; 522/135; 522/136; 522/137; 522/145; 522/146; 523/105; 523/106; 525/54.1; 526/238.1

[58] Field of Search ............... 527/201, 202; 522/135, 522/136, 137, 145, 146; 523/105, 106; 525/54.1; 526/238.1

[56] References Cited

U.S. PATENT DOCUMENTS 4,687,820 8/1987 Hou et al. ........................... 525/54.1

Primary Examiner—Nathan M. Nutter
Attorney, Agent, or Firm—Burgess, Ryan & Wayne

[57] ABSTRACT

A biocompatible material which is the product of graft-copolymerization of a water-soluble vinyl and/or an acrylate monomer with a sorption complex of polysilicic acid and collagen that has been rid of pigments, glycoproteins and proteoglycans, or a product obtained by virtue of chemical destruction, with the aid of hydrofluoric acid, of the afore-mentioned product of graft-copolymerization, containing up to 25 mass percent of polysilicic acid (in terms of $SiO_2$), up to 12 mass percent of protein, and maximum $1 \cdot 10^{-6}$ mole/g of an anion of hydrofluoric and hydrofluoric acids, methods of making the same and products produced thereby.

21 Claims, No Drawings

BIOCOMPATIBLE POLYMER MATERIAL AND A PROCESS FOR PRODUCING SAME

FIELD OF THE INVENTION

The present invention relates generally to medicine and more specifically to a novel biocompatible polymer material and to a process for producing same, said material finding application in ophthalmology for making contact lenses, allodrains, biofillings, for intrastromal lenses, and other items.

BACKGROUND OF THE INVENTION

A number of diverse biocompatible materials are known to use in ophthalmological practice, which are based on collagen, i.e., fibrous protein. Collagen serves as a kind of framework performing a supporting function for other proteins, as well as for cells; it is present in all body tissues, in the skin, tendons, and bones.

A variety of techniques of collagen isolation from raw materials are widely known, by its dissolution in acids, alkalis, salts, or with the aid of enzymes, as well as its isolation in a solid undissolved fibrous state by exposing the disintegrated raw material to the effect of salts. The isolated collagen is cleaned from pigments, glycoproteins, and proteoglycans, using the commonly known methods.

One state-of-the-art biocompatible collagen-based material is known to use for making contact lenses (U.S. Pat. No. 4,268,131), said material being in fact a gel based on fibrous collagen or a mixture of fibrous collagen with collagen in a dissolved state.

In order to produce said material diverse methods are used for collagen extraction from raw stock (such as hides, tendons, skin, and others) by means of its dissolution in acids (acetic or citric) or in alkalis, followed by centrifugation of the resultant solution, washing it with water, dehydration, drying, redissolution, filtration, precipitation, and recentrifugation. To produce a lens, a 4- to 10-percent gel is prepared on the basis of collagen in an aqueous acid medium having the pH value of from 2 to 4. Resort is also made to enzymic extraction in the presence of proteolytic enzymes, such as pepsin, trypsin, protease, and others.

However, the aforesaid material cannot be used for making long-lived transplants and those having preset porosity of the material, and hence its gas permeability, since used for producing said material is a protein that features a statistical average mass of from 120 to 130 thousand D (the porosity of the material depends on the geometric dimensions of a molecule and the physicochemical characteristics of collagen by which said material is constituted).

Moreover, the material in question is not resistant to the effect of enzymes as being completely constituted by protein molecules, which are liable to undergo lysis. Thus, low porosity of the material and its low resistance to the effect of enzymes result in reduced biocompatibility of the material with the eve tissues.

Another prior-art collagen-based biological material containing ethylene-unsaturated compounds is known to use for making contact lenses (U.S. Pat. No. 4,388,428).

The material under consideration is in effect a polymerized hydrophilic composition liable to swell in water and consisting of soluble collagen and an ethylene-unsaturated monomer featured by the presence of a polymerizable double carbon-carbon bond.

The material discussed herein is produced by extracting fibrous collagen from animal's hide by enzymic extraction with the aid of pepsin. The thus-extracted and purified collagen is mixed with an aqueous solution of an ethylene-unsaturated monomer, and in the resultant mixture collagen is dissolved by acidifying said mixture with 1.0M HCl till the pH value of 3. The resultant solution is filtered, drawn in a syringe, wherein the solution is degassed, centrifugated and filled into lens moulds.

However, the material dealt with in the form of a hydrogel is featured by inadequate gas permeability and porosity accounted for by geometric dimensions of collagen molecules and of molecules of the monomer used, as well as by a low protein content, low shelf- and service life.

SUMMARY OF THE INVENTION

It is an object of the present invention to provide a material possessing high gas permeability and porosity, as well as biocompatibility, mechanical strength, and a high optical refractive index.

It is another object of the present invention to provide a process for producing the herein-proposed material.

The foregoing principal and further objects are accomplished due to the fact that proposed herein, according to the invention, is a biocompatible polymer material, which is in fact a highly porous material, i.e., the product of graft-copolymerization of a water-soluble vinyl and/or acrylate monomer with a sorption complex of polysilicic acid and collagen that has been preliminarily purified of pigments, glycoproteins, and proteoglycans, or a product obtained by way of chemical destruction, with the aid of hydrofluoric acid, of said product of graft-copolymerization, containing up to 25 weight percent of polysilicic acid (in terms of $SiO_2$), up to 12 weight percent of protein, and maximum $1 \cdot 10^{-6}$ mole/g of an anion of hydrofluorosilicic and hydrofluoric acids.

The proposed material features high gas permeability and porosity, its gas permeability being 3- to 6 times that of a known material of the charecter set forth hereinabove.

High porosity of the proposed material is responsible for its higher elasticity, which in turn adds to its biocompatiblity. Besides, products made of the proposed material are three times more biocompatible when compared to a known material (U.S. Pat. No. 4,268,131) also due to poor adhesion of the cells of the macrophagocytic series. Thus for instance, adhesion of cells in the proposed material equals $10^2$ per square centimeter, whereas that in a known material (U.S. Pat. No. 4,268,131) is equal to $10^6$ per square centimeter.

The proposed material is also featured by a high optical refractive index and mechanical strength, as well as by high resistance to the effect of proteolytic enzymes.

A process for producing the proposed material, according to the invention, resides in that an acid solution of collagen isolated from the eyeball sclera of farm animals and rid of pigments, glycoproteins, and proteoglycans, is mixed with an aqueous solution of an alkali polysilicate, or with polysilica gel to a pH value of from 4.5 to 6.0 to form a sorption polymer of polysilicic acid, whereupon the thus-obtained sorption polymer is cleaned from cations and subjected to graft-copolymerization with a water-soluble vinyl and/or acrylate monomer while being exposed to the effect of radiation in the dosage of 0.5 to 1.5 Mrad, followed by isolation of the end product.

Prior to isolation of the end product the thus-obtained product of graft-copolymerization may be treated with hydrofluoric acid and be electrochemically purified of cations and anions. 2-Hydroxyethylmethacrylate, or acrylamide, or else N-vinylpyrrolidone, or a mixture thereof is used preferably as a water-soluble vinyl and/or acrylate monomer.

The proposed process makes it possible to produce a novel biocompatible polymer material posessing high gas permeability, biocompatibility, mechanical strength and optical refractive index.

DETAILED DESCRIPTION OF THE INVENTION

The proposed polymer material has been tested for biocompatibility as against adhesion of the cultural cells of the fibroplastic and macrophagocytic series (on a culture of keratocytes and peritoneal macrophagocytes).

To this aim, pieces of the material measuring 20×20 mm were placed in a culture medium, whereupon a suspension of cells was introduced thereinto. It has been established, as a result of the experiments performed, that corneal fibroplastic cells adhere well (80 to 90 percent of a total amount of such cells) and spread flat on the proposed material, whereas no cells of the inflammatory series practically adhere to the surface of said material. A run of experiments was condusted, wherein the contact lenses made from the proposed material were placed onto the cornea. A total of 30 test rabbits were employed in the experiments. The state of biocompatibility was assessed by the presence of the conjuctival edema. No edematous manifestations were noticed from the instant when the lens had been placed onto the rabbit's eye. Clinical trials of the proposed material have demonstrated its good permeability to oxygen and biocompatibility.

The proposed process for producing the biocompatible polymer material of the invention is carried into effect as follows.

Collagen extraction from the raw material and its getting rid of pigments, glycoproteins and proteoglycans can be effected using any of the heretofore-known techniques.

The procedure may, e.g., be as follows. The eyeball sclera of farm animals is carefully cleaned of the internal eyeball tunics and conjunctival and muscular reqidues, whereupon the stroma is excised. Then the pigments are completely eliminated, which can be attained by concurrent mechanical or enzymic treatment, the latter procedure making it possible to completely remove the pigmental layer. The treatment is carried out as follows: pieces of the untreated sclera are placed in a weekly acidified isotonic sodium chloride solution, or in an acetic acid solution (pH being from 4.5 to 6.0), then some trypsin is added to the solution (0.01 g per gram of dry sclera) and treatment occurs at 37° C. for two hours under constant stirring. Then the sclera is removed from the solution and washed with distilled water (one gram of dry sclera per 10 to 15 l of water) under constant stirring. The pigment residues are removed mechanically and the stroma is cut into small pieces. Next the mass is thoroughly washed in distilled water till complete elimination of mechanical impurities and blood, transferred in a flask and a 10-percent sodium hydroxide solution is added thereto (500 ml of the solution per 10 kg of the tissue), whereupon the solution is allowed to stand for 48 hours at 18° to 36° C. Next the solution is poured out and the tissue is neutralized till the pH value of 6.8 to 7.0 by placing it in a 2-percent boric acid solution, while constantly stirring and regulatory changing the solution. Thereupon the tissue is washed with distilled water till complete elimination of sulfate ion from the wash liquid and a 1M acetic-acid solution is added thereto so that the final collagen concentration in the solution be in excess of one percent. Then the mass is stirred and kept in a cooler for one or two days at 4° C., after which it is homogenized, centrifugated at 3000 rpm for 30 minutes and left for 24 hours at 4° C. The resultant solution is passed through a glass filter, whereupon collagen is subjected to an additional treatment with trypsin in a 1M acetic-acid solution, the trypsin proportion being the same as in the preceding case (i.e., 0.01 g of trypsin per gram of dry sclera) and the treatment time being one hour at 37° C. The resultant solution is passed through an unglazed-porcelain filter so as to eliminate the entire trypsin and to let collagen remain in the solution, the washing-out of trypsin being carried out with the aid of an acetic acid solution. Next the collagen solution is concentrated, by passing it through an unglazed-porcelain filter, to a concentration range of from 1 to 10 weight percent. Use may be made of solutions of some other diluted acids, such as formic or hydrochloric for preparing collagen solutions.

Then the thus-prepared acid collagen solution is mixed, under constant stirring, with an aqueous alkali salt. Stirring ceases as soon as the pH value of 4.5 to 6.0 is attained and a sorption polymer of polysilicic acid is formed. The acid collagen solution can also be mixed with a preliminarily prepared gel of polysilicic acid. The resultant mixture is also stirred till the pH value of 4.5 to 6.0 is attained and said sorption polymer of polysilicic acid is established.

The thus-produced sorption polymer is allowed to stand for 24 hours at +4° C. under constant stirring, whereupon it is centrifugation-concentrated and cleaned of cations.

The resultant sorption polymer is saturated with water-soluble monomers, such as acrylamide, vinylpyrrolidone, or others, or with mixtures thereof. The saturation procedure occurs as follows. The sorption polymer is disintegrated in the monomer and kept therein for 24 hours, whereupon the surplus monomer is filtered out. The resultant mixture is cooled down to 0° C. and exposed to the effect of radiation with a dose of from 0.5 to 1.5 mrad. The radiation graft-copolymerization is carried out with a radiation dose within the aforesaid range, since the lower radiation dosage fails to yield the material having an adequately high mechanical strength. On the other hand, a dose of 1.5 mrad is an upper limit, since higher doses of radiation fail to add to the mechanical strength of the material. The end product, whenever it becomes necessary, is dried and subjected to mechanical treatment to produce optical articles therefrom, such as contact lenses. After having been treated with radiation the resultant product of graft-copolymerization may be treated with hydrofluoric acid. To this end, the thus-obtained product of graft-copolymerization is placed in a solution of chemically pure hydrofluoric acid and left therein for 24 hours, whereupon the resultant product is cleaned electrochemically of cations and anions.

The electrochemical cleaning is ceased not until complete elimination of surplus ions of $F^-$ and $SiF_6^{-2}$ from the end product, since said ions are causative, when in certain quantitative concentrations, of an inflammatory reaction within the first days following the start of application of the proposed material.

To promote understanding of the present invention given below are the following examples illustrating the various embodiments of the proposed material, of the process for its production, and of its evaluation.

EXAMPLE 1

40 g of cleaned and washed scleral stroma is placed in one liter of 0.1M acetic acid, 0.1 g of trypsin is added thereto, and the solution is allowed in incubate at 37° C. for an hour, whereupon the sclera is washed in 10 l of distilled water. The pigment residues are removed mechanically, and the stroma is cut to pieces, and added thereto is 2 l of 10-percent sodium hydroxide, whereupon the solution is kept for 48 hours at 18° to 20° C. after which the solution is poured out. The tissue is washed with a small amount of distilled water, 2 l of a 2-percent aqueous boric acid solution is added thereto and the result- and solution is subjected to agitation in a magnetic stirrer for two hours, while changing the boric acid solution two-fold. While being constantly stirred the tissue is carefully washed with 5 l of distilled water till complete elimination of the sulfate ion from the wash liquid, 700 ml of 0.5M acetic acid is added thereto, and the solution is allowed to stand for 24 hours at 4° C. Next the mass is homogenized with the aid of a mechanical tissue comminuter, centrifugated at 3000 rpm for 30 minutes and held for three days at 4° C. The resultant solution is passed through a glass filter. Then trypsin is added to the resultant collagen solution (0.1 g per 1200 ml of the solution) and the mixture is subjected to incubation for one hour, whereupon the resultant solution is passed through an unglazed-porcelain filter and doped with 10 l of 0.1M acetic acid till the collagen concentration of 4 weight percent in the solution is obtained. The thus-obtained acid collagen solution is added dropwise, under constant stirring; to a 20-percent sodium silicate ($Na_2SiO_3$) solution that has been passed through a 0.22-filter. Then the solution is mixed till the pH value of 6.0 and the formation of a gel-like sorption polymer of polysilicic acid. The thus-obtained polymer is left to stay at 4° C. for 24 hours, then excess water is separated therefrom, and the polymer is centrifugated at 3000 rpm for 30 minutes. The resultant polymer is disintegrated in one liter of deionized water and centrifugated at 3000 rpm, the procedure being repeated sixfold. Then added to 100 g of the resultant sorption polymer is 700 g of 2-hydroxyethylmethacrylate, the sorption polymer is disintegrated in the monomer solution, and centrifugated at 3000 rpm for 30 minutes. The resultant mixture is transferred into a mould, cooled down to 4° C., exposed to the effect radiation with a dose of 1.5 Mrad, and dried. The resultant material is in effect of graft-copolymer or 2-hydroxyethylmethacrylate and the sorption complex of polysilicic acid and collagen, featuring the polysilicic acid content of 15.6 weight percent in terms of $SiO_2$, and the protein content of 11.4 weight percent.

A contact lens made from the proposed material was held to the patient's corneal surface, with the result that the corneal edema on the second-third day was as low as 0.1 percent, which is indicative of good permeability of the proposed material to oxygen and of its biocompatibility.

EXAMPLE 2

The graft-copolymer of 2-hydroxyethylmethacrylate and a sorption complex of polysilicic acid and collagen is prepared in a way similar to Example 1, which graft-copolymer is then treated with a 0.4-percent hydrofluoric acid solution for 24 hours at 25° C., then placed in deionized water (10 g per liter of water) and the procedure is repeated sixor sevenfold, whereupon the material is transferred into an electrochemical bath and subjected to electrochemical purification in a $10^{-3}M$ aqueous hydrochloric acid solution of ions of $F^-$ and $SiF_6^{-2}$ at a voltage of 300 V and a power input of 8 W. Then the material is washed off hydrochloric acid in deionized water (one gram of the material per 10 l of water), then in a phosphate buffer to obtain the material which is in fact the product of chemical destruction, with the aid of hydrofluoric acid, of the graft-copolymer of 2-hydroxyethylmethacrylate and a sorption complex of polysilicic acid and collagen, having the pore size of from 0.025 to 0.35 μm. The material is free from polysilicic acid and features the protein content of 12.0 weight percent, and that of the anion if hydrofluorosilicic and hydrofluoric acids of $1 \cdot 10^{-6}$ mole/g.

A contact lens made from the proposed material, when evaluated, exhibited the results similar to Example 1.

EXAMPLE 3

The process is conducted as in Example 1 with the sole exception that the resultant collagen solution is diafiltered with 10 l of 0.5M acetic acid till a collagen concentration of 35 weight percent. The resulting acid collagen solution is added dropwise under constant stirring to a 35-percent sodium silicate ($Na_2SiO_3$) solution that has preliminarily been passed through a 0.22 μm filter. The solution is mixed until a gel-like sorption polymer of polysilicic acid is obtained. Then the thus-produced polymer is allowed to stand at 0° C. for 24 hours, after which the excess water is separated therefrom, and the polymer is centrifugated at 3000 rpm for 30 minutes. Next the sorption polymer is disintegrated in a microcomminuter in one liter of deionized water, the pH value being 6.5, the procedures being repeated six- to eightfold till complete elimination of the cations of metals, which is monitored on a flame photometric analyzer. Then added to 100 g of the obtained polymer is 800 g of a mixture, consisting of 600 g of acrylamide, 0.1 g of N-methylenebisacrylamide, water being the balance. The polymer is then disintegrated in a microcomminuter in a monomer solution, and the resultant pulp is centrifugated at 3000 rpm for 30 minutes. The thus-obtained mixture is transferred into a mould, cooled down to 0° C. and exposed to the effect of gamma-radiation in a dose of 0.5 Mrad. The result is a material, which is in fact the graft-copolymer of acrylamide and a sorption complex of polysilicic acid and collagen, featuring the polysilicic acid content of 24.0 weight percent in terms of $SiO_2$, and the protein content of 10.2 weight percent.

An intrastromal plate made from the proposed material was implanted into the corneal layers. No response to the material was observed, the corneal layers were transparent on the second-fourth month after implantation, which was indicative of good permeability and biocompatibility of the material. No fibroplastic reaction to the implanted material was found at the corneal histological microsections.

EXAMPLE 4

The graft-copolymer of acrylamide and a sorption complex of polysilicic acid and collagen is obtained as in Example 3, which is treated with a 0.4-percent hydrofluoric acid solution for 24 hours at 25° C., then placed in deionized water (10 g per liter of water), and the procedure is repeated several fold, whereupon the material is placed in an electrochemical bath and subjected to electrochemical purification, in a $10^{-3}$ M aqueous hydrochloric solution, of the ions of $F^-$ and $SiF_6^{-2}$ at a voltage of 300 V and a power input of 8 W for 3 hours. Next the material is washed, to get rid of hydrochloric acid, first with deionized water, then in a phosphate buffer. The result is a material, which is in fact the product of chemical destruction, with the aid of hydrofluoric acid, of the graft-copolymer of acrylamide and a sorption complex of polysilicic acid and collagen, featuring the pore size of from 0.025 to 2.0 μm, the zero content of polysilicic acid, the protein content of 10.6 weight percent, and the content of the anion of hydrofluorosilicic and hydrofluoric acids of $5 \cdot 10^{-7}$ mole/g.

A contact lens made from the proposed material, when tested, exhibited the results similar to Example 3.

EXAMPLE 5

The process is carried out similarly to Example 1, with the sole exception that the resultant acid collagen solution is diafiltered with 10 l of a 0.5M solution of hydrochloric acid till a collagen concentration of 11 weight percent is attained. The thus-obtained collagen solution is added dropwise, under constant stirring, to a 10-percent solution of sodium silicate ($Na_2SiO_3$) that has preliminarily been passed through a 0.22 μm filter. Then the solution is mixed till the pH value of 4.5 is attained and a gel-like sorption polymer of polysilicic acid is established, and the thus-obtained polymer is allowed to stand at 4° C. for 24 hours. Next the excess water is separated and the polymer is centrifuged at 3000 rpm for 30 minutes. The sorption polymer is disintegrated in a microcomminuter in one liter of deionized water having the pH value of 6.5, the procedure is repeated six- or eightfold till the complete elimination of the cations of metals, which is monitored on a flame photometric analyzer. Then added to 100 g of the thus-produced polymer is a mixture, consisting of 300 g of 2-hydrozyethylmethacrylate and 100 g of N-vinylpyrrolidone, the polymer is disintegrated in a monomer solution and centrifuged at 3000 rpm for 30 minutes. The resultant mixture is transferred into a mould, cooled down to 0° C. and exposed to the effect of radiation in a dose of 1.0 Mrad. The obtained material is dried. The thus-produced material is in fact the graft-copolymer of 2-hydroxyethylmethacrylate and N-vinylpyrrolidone, and a sorption complex of polysilicic acid and collagen, the polysilicic acid content being 8.0 weight percent in terms of $SiO_2$, and the protein content, 6.2 weight percent.

A transplant made from the proposed material in the form of a disk having a diameter of 6 mm and a thickness of 0.2 mm was implanted into the corneal layers. No response to the material was observed, the corneal layers were transparent on the second-third month after implantation, which was indicative of good permeability of the material of oxygen and glucose, as well as good biocompatibility.

EXAMPLE 6

The graft-copolymer of 2-hydroxyethylmethacrylate and N-vinylpyrrolidine and a sorption complex of polysilicic acid and collagen is produced as in Example 5, which is treated with a one-percent hydrofluoric acid solution for 24 hours at 25° to 30° C. and then placed in deionized water (10 g per liter of water), the procedure is repeated six- or seven-fold, whereupon the material is transferred into an electrochemical bath and subjected to electrochemical purification of the ions of $F^-$ and $SiF_6^{-2}$ at a voltage of 300 V and a power input of 9 W for 3 hours. Then the material is washed off hydrochloric acid in deionized water (1 g per 10 l of water), then washed with a phosphate buffer, packed and sterilized.

The result is the material, which is in fact the product of chemical destruction, with the aid of hydrofluoric acid, of the graft-copolymer of 2-hydroxyethylmethacrylate and a sorption complex of polysilicic acid and collagen, having the pore size of from 0.025 to 0.13 μm, free from polycilicic acid and featuring the protein content of 6.5 weight percent and the content of the anion of hydrofluorosilicic and hydrofluoric acids of $8 \cdot 10^{-7}$ mole/g.

An intrastromal lens made from the proposed material was implanted into the corneal layers of a test rabbit's eyeball. No response to the material was observed, the corneal layers were transparent on the second and third months after implantation, which was indicative of good permeability and biocompatibility of the material.

EXAMPLE 7

The process is carried out similarly to Example 5, the sole exception that the resultant acid acid collagen solution is diafiltered with 10 l of a 0.5M solution of hydrochloric acid till the collagen concentration of 11 weight percent is attained. The thus-obtained collagen solution is added dropwise, under constant stirring, to the polysilicic gel resulting from precipitating, with the aid of hydrochloric acid, a 20-percent aqueous sodium silicate solution. The resultant material is similar to that of Example 5.

The proposed biocompatibility polymer material possesses high gas permeability, which is three- to six-time that of the heretofore-known material. High porosity of the proposed material adds to its elasticity, which in turn renders the material more biocompatible, that is, biocompatibility of articles made from the proposed material is threefold higher than that of the heretofore-known material. The proposed material also features high optical refractive index and mechanical strength.

What we claim is:

1. A biocompatible polymer comprising the product of the graft-copolymerization of a water-soluble monomer selected from a vinyl monomer, an acrylate monomer, and mixtures thereof, with a sorption complex of polysilicic acid and collagen that has been pretreated to remove pigments, glycoproteins, and proteoglycans, said graft-copolymerization product containing up to 25 weight percent of polysilicic acid measured in terms of $SiO_2$ and up to 12 weight percent of protein.

2. The biocompatible polymer of claim 1 wherein the copolymerization product is further treated with hydrofluoric acid to obtain a biocompatible polymer containing a maximum of $10^{-6}$ mole/g of hydrofluorosilicic and hydrofluoric acid.

3. The biocompatible polymer of claim 1 obtained by forming an acid solution of collagen, mixing said acid solution of collagen with a reagent selected from the group consisting of an aqueous solution of an alkali polysilicate and polysilica gel until the combined solution reaches a pH of from 4.5 to 6.0 to thereby form a sorption polymer of polysilicic acid, removing cations from said polymer and graft-copolymerizing said polymer with said water-soluble monomer under radiation in a dosage of 0.5 to 15 Mrad.

4. The biocompatible polymer of claim 3 wherein the irradiated material is isolated.

5. The biocompatible material polymer of claim 1 which is highly porous.

6. A contact lens comprising the biocompatible polymer of claim 1.

7. A contact lens comprising the biocompatible polymer of claim 2.

8. A contact lens comprising the biocompatible polymer of claim 3.

9. A contact lens comprising the biocompatible polymer of claim 4.

10. A process for producing a biocompatible polymer comprising mixing an acid solution of collagen with a reagent selected from the group consisting of an aqueous solution of an alkali polysilicate and polysilica gel until the combined solution reaches a pH of from 4.5 to 6.0 to thereby form a sorption polymer of polysilicic acid, removing cations from said polymer and graft-copolymerizing said polymer with a water-soluble monomer selected from the group consisting of a vinyl monomer, an acrylate monomer, and mixtures thereof.

11. The process of claim 10 further comprising treating the graft-copolymer with hydrofluoric acid to obtain a biocompatible polymer having a maximum of $10^{-6}$ mole/g of hydrofluoro silicic and hydrofluoric acid.

12. The process of claim 11 further comprising removing anions from the graft-copolymer by electrochemical means.

13. The process of claim 10 further comprising reacting the graft-copolymer with said water-soluble monomer under radiation at a dosage of from 0.5 to 15 Mrad.

14. The process of claim 13 further comprising isolating the end product after said irradiation step.

15. The process of claim 10 wherein a water-soluble monomer is a monomer selected from the group consisting of 2-hydroxyethylmethacrylate, acrylamide, N-vinylpyrrolidone, and mixtures thereof.

16. The product produced by the process of claim 10.
17. The product produced by the process of claim 11.
18. The product produced by the process of claim 12.
19. The product produced by the process of claim 13.
20. The product produced by the process of claim 14.
21. The product produced by the process of claim 15.

* * * * *